March 12, 1974 H. HOLTKAMP Plant Pat. 3,516
AFRICAN VIOLET
Filed Aug. 24, 1972
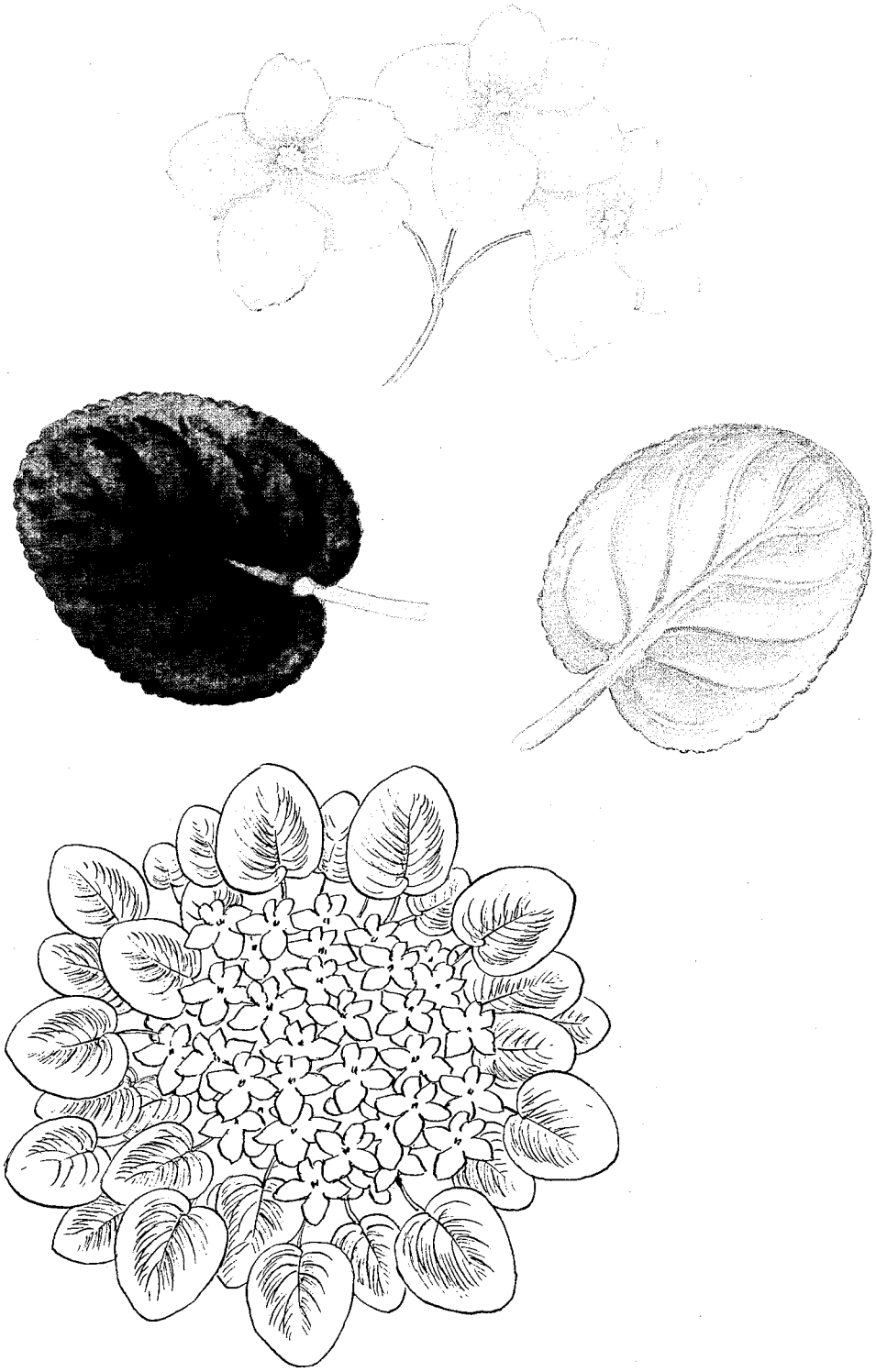

United States Patent Office

Plant Pat. 3,516
Patented Mar. 12, 1974

3,516
AFRICAN VIOLET

Hermann Holtkamp, Werther Strasse 5–7, Postfach 19, 4234 Isselburg, Germany

Filed Aug. 24, 1972, Ser. No. 283,587
Int. Cl. A01h 5/00
U.S. Cl. Plt.—69 1 Claim

ABSTRACT OF THE DISCLOSURE

A hybrid violet of a descendant of a cross between *Saintpaulia ionantha* and *Saintpaulia shumensis* species which has permanent characteristics including strength of stem, fast and vigorous growth, profuse flowering, uniform bouquet, prolonged blooming period, resistance to disease, reliability in initiating new plantlets, retention of flowers past maturity on their respective stems, and uniformity throughout the life cycle.

BRIEF SUMMARY

The present new variety was originated by me by crossing an unpatented African violet variety, "Rhapsodie Pink," Type 10/23 with another unpatented African violet, "Rhapsodie Light Pink," Type 9/68. Both of these varieties were devolped by me as the result of an extensive breeding program, and the plants had substantially the same general physical characteristics as "Rhapsodie Gisela," disclosed in my United States Letters Pat. No. PP 3,053 of Apr. 20, 1971, apart from color and the larger size of individual flowers.

In the present variety the individual flowers are large and a very light pink with darker centers around the anthers and the petals have stripes of darker hue or shade radiating from the center. The plants themselves have generally the same physical characteristics as the plants disclosed in the above-designated patent, in their strength of stem, profuse flowering, uniform bouquet, prolonged blooming period, resistance to disease, reliability and uniformity. The color and size of the individual flowers are the principal features that distinguish this variety from those of the variety shown in said patent.

DESCRIPTION OF DRAWINGS

The upper illustrations show, in full color, several of the flowers; and the opposite sides of one of the leaves; and below, in pen and ink, a top plan view in reduced size of a plant showing a flower head and a wreath of leaves therearound.

DESCRIPTION OF DRAWINGS

Name: "Rhapsodie" Gloria
Male parent: "Rhapsodie" Pink Type 10/23
Female parent: "Rhapsodie" Light Pink Type 9/68
Plants: 5 to 6 inches tall
Leaves: Borne in rosette arrangement from 10 to 12 inches in diameter
- *Shape.*—Round to oval, slightly scalloped along edge
- *Length.*—3½ to 4½ inches
- *Width.*—2½ to 3½ inches
- *Upper side.*—Slightly hairy
- *Underside.*—Slightly hairy
- *Color.*—Upper side medium green. Underside light green to reddish along veins Petiole: Round
Flowers: Borne profusely in large, central upright flower head above foliage
Individual flowers: Quinquepartite, bilaterally symmetrical
- *Size.*—2 to 2½ inches in diameter
- *Color.*—Light pink, darker center and radial stripes of slightly darker hue on petals
- *Calyx.*—Quinquepartite
- *Peduncles.*—Multiflorous, 8 to 12 flowers Genital organs:
- *Stamens.*—Two fructified
- *Anthers.*—Light yellow
- *Ovary.*—Pilous
- *Seed capsule.*—Does not push through Roots: Well developed root system, white when young, turning to a brownish color on older plants.

The color designations, according to "Dictionary of Color" by Maerz and Paul are as follows:

| | Plate | Letter | No. |
|---|---|---|---|
| Body of leaf: | | | |
| Upper side medium green | 23 | C | 6 |
| Underside, light green, reddish along veins | 20 | A | 3 |
| Petiole | 6 | J | 9 |
| Main body of flower: | | | |
| Light pink petals | 41 | D | 2 |
| Faint radial stripes | 41 | F | 3 |
| Darker pink at base of two smaller petals | 41 | K | 5 |
| Anthers | 9 | L | 4 |

GENERAL CHARACTERISTICS

There may be minor variations in the leaf size, shape and color, and in the shape of the flowers, which variations are common to African violets, but there is substantial uniformity in all the other characteristics described in the aforesaid patent. Thus in the present variety the characteristics that are constant and that distinguish it from the other varieties include: the large, central, upright flower head within and above a wreath of green leaves of a rosette arrangement relative to the flower head; and large individual flowers of light pink with a darker pink at the base of the petals, and which petals have faint radially extending stripes of a slightly darker shade than the color of said light pink color.

I claim:

1. A distinct variety of African violet substantially as herein shown and described, characterized by a habit of bearing a large, central, upright flower head within and above a wreath of green leaves extending around said flower heads, and the individual flowers of which are from approximately 2 to 2½ inches in diameter with very light pink petals having faint radially extending stripes, with the bases of the two smaller petals a deeper pink adjacent central light yellow anthers.

No references cited.

ROBERT E. BAGWILL, Primary Examiner